(12) United States Patent
Silver et al.

(10) Patent No.: US 7,616,316 B1
(45) Date of Patent: Nov. 10, 2009

(54) GAS MEASUREMENT OVER EXTREME DYNAMIC RANGE OF CONCENTRATIONS

(75) Inventors: Joel A. Silver, Santa Fe, NM (US);
Mark E. Paige, Santa Fe, NM (US);
David S. Bomse, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 320 days.

(21) Appl. No.: 11/679,608

(22) Filed: Feb. 27, 2007

Related U.S. Application Data

(60) Provisional application No. 60/777,329, filed on Feb. 27, 2006.

(51) Int. Cl.
G01N 21/00 (2006.01)

(52) U.S. Cl. .................. 356/437; 356/409

(58) Field of Classification Search ........... 356/244, 356/246, 432–440, 409; 250/343, 576
See application file for complete search history.

(56) References Cited

U.S. PATENT DOCUMENTS

| 4,297,035 | A | | 10/1981 | Bjorklund |
| 4,507,558 | A | | 3/1985 | Bonne |
| 4,520,265 | A | | 5/1985 | Griggs et al. |
| 4,765,736 | A | | 8/1988 | Gallagher et al. |
| 4,934,816 | A | * | 6/1990 | Silver et al. ............ 356/409 |
| 5,134,276 | A | | 7/1992 | Hobbs |
| 5,570,697 | A | * | 11/1996 | Walker et al. ............ 600/532 |
| 6,005,661 | A | | 12/1999 | Machler |
| 6,031,609 | A | | 2/2000 | Funk et al. |
| 6,188,474 | B1 | | 2/2001 | Dussault et al. |
| 6,643,016 | B2 | | 11/2003 | Garver et al. |
| 7,075,653 | B1 | | 7/2006 | Rutherford |
| 7,134,999 | B2 | | 11/2006 | Brauker et al. |
| 2003/0010941 | A1 | * | 1/2003 | Spolaczyk et al. ............ 250/573 |
| 2004/0065816 | A1 | * | 4/2004 | Ye et al. ............ 250/227.18 |

OTHER PUBLICATIONS

Bjorklund, G. C., et al., "Frequency Modulation (FM) Spectroscopy", *Applied Physics B*, vol. 32, Springer-Verlag,(1983),145-152.
Bomse, David S., et al., "Frequency Modulation and Wavelength Modulation Spectroscopies: Comparison of Experimental Methods Using a Lead-Salt Diode Laser", *Applied Optics*, vol. 31, No. 6, (Feb. 20, 1992),718-731.
Chen, Hui , et al., "Near-infrared saturation spectroscopy of cesium molecules using a diode laser", *J. Opt. Soc. Am. B*, vol. 23, No. 4,(Apr. 2006),723-726.

(Continued)

*Primary Examiner*—Hoa Q Pham
(74) *Attorney, Agent, or Firm*—Jeffrey D. Myers; Peacock Myers, P.C.

(57) ABSTRACT

An optical spectroscopy apparatus and method for measurement of species concentration, number density, or column density comprising emitting light from a laser light source, receiving light via a fixed length optical path from the source and containing a species to be detected, receiving light via a detector at an end of the path, determining one or more of species concentration, number density, and column density via signal processing electronics connected to the detector, and switching between a plurality of operational modes measuring a same absorption feature of the species depending on measured absorbance.

22 Claims, 6 Drawing Sheets

OTHER PUBLICATIONS

Drayson, S. R., "Rapid Computation of the Voigt Profile", *J. Quant. Spectrosc. Radiat. Transfer,* vol. 16, Pergamon Press, Great Britain,(1976),611-614.

Frish, M.B. , et al., "Standoff gas leak detectors based on tunable diode laser absorption spectroscopy", *SPIE Optics East,* Boston, MA., Society of Photo-Optical Instrumentation Engineers,(Oct. 23, 2005).

Herriott, Donald R., et al., "Folded Optical Delay Lines", *Applied Optics,* vol. 4 No. 8 (Aug. 1965),883-889.

Hui, A. K., et al., "Rapid Computation of the Voigt and Complex Error Functions", *J. Quant. Spectrosc. Radiat. Transfer,* vol. 19, Pergamon Press, Great Britain,(1978),509-516.

Rothman, L. S., et al., "The HITRAN 2004 molecular spectroscopic database", *Jounral of Quantitative Spectroscopy & Radiative Transfer,* vol. 96, Elsevier,(2005),139-204.

Sanders, Scott T., et al., "Rapid temperature tuning of a 1.4-um diode laser with application to high-pressure H2) absorption spectroscopy", *Optics Letters,* vol. 26, No. 20, Optical Society of America,(Oct. 15, 2001),1568-1570.

Silver, Joel A., "Frequency-Modulation Spectroscopy for Trace Species Detection: Theory and Comparison Among Experimental Methods", *Applied Optics,* vol. 31, No. 6, (Feb. 20, 1992),707-717.

Svanberg, S. , et al., "Saturation spectroscopy for optically thick atomic samples", *J. Opt. Soc. Am. B,* vol. 4, No. 4, Optical Society of America,(Apr. 1987),462-469.

White, John U., "Long Optical Paths of Large Aperture", *Journal Optical Society Am.,* vol. 32, (May 1952),285-288.

Cooper, D. E. et al., "Double Frequency Modulation Spectroscopy", *Appl. Opt.* vol. 24 1985 , 1327-1333.

Hirschfield, T. et al., "Dynamic range improvement in Fourier transform infrared spectroscopy", *J. Am. Chem. Soc.* vol. 50 1978, 1227-1228.

Hobbs, P.C. D. et al., "Ultrasensitive laser measurements without tears", *Appl. Opt.* vol. 36 1997 , 903-920.

Reid, J. et al., "Sensitive limits of a tunable diode laser spectrometer with application to the detection of NO2 at the 100-ppt level", *Appl. Opt.* vol. 19 1980 , 3349-3354.

Silver, J. A. et al., "Two-Tone Optical Heterodyne Spectroscopy Using Buried Double Heterostructure Lead-Salt Diode Lasers", *Appl. Opt.* vol. 27 1988 , 4438-4444.

Zondlo, M. A. et al., "VCSEL-based hygrometer for the High-performance Instrumented Airborne Platform for Environmental Research (HIAPER)", *American Chemical Society National Meeting, Paper No. 302, Analytical Chemistry, Analytical Chemistry in the Atmospheric Sciences* San Diego, California Mar. 14, 2005.

\* cited by examiner

GAS MEASUREMENT OVER EXTREME DYNAMIC RANGE OF CONCENTRATIONS

CROSS-REFERENCE TO RELATED APPLICATIONS

This application claims priority to and the benefit of the filing of U.S. Provisional Patent Application Ser. No. 60/777,329, entitled "Gas Measurement Over Extreme Dynamic Range of Concentrations", filed on Feb. 27, 2006, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to optical absorption spectroscopy, particularly over an extreme dynamic range of concentrations.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Optical absorption spectroscopy can be used for quantitative measurements of the concentrations or number densities of gases, liquids, and solids. The underlying theory, identified as Beer's Law or the Beer-Lambert Law, relates the change in intensity of a light beam as it passes through a sample to the sample's optical absorbance:

$$\frac{I}{I_0} = e^{-n\sigma l}$$

where I is the light beam intensity after passing through the sample, $I_0$ is the light beam intensity before encountering the sample, n is the target species concentration or number density, $\sigma$ is the species absorption cross section, and l is the length of the optical path through the sample. The ratio $I/I_0$ is the transmission, and is expressed as a fraction between 0 and 1, or as a percentage between 0 and 100%. The product, $n\sigma l$, is the optical absorbance, $\alpha$, and is a dimensionless quantity. The target species concentration or number density, n, is readily determined from a measured sample absorbance, $\alpha$, because the absorption cross section, $\sigma$, is a physical property of the target species and can be determined prior to investigating the sample, and the optical path length, l, is a design parameter of the optical absorbance measuring apparatus. Such types of apparatus include but are not limited to spectrometers including laser based spectrometers and spectrophotometers. The concentration can also be expressed as a mole fraction.

The measurement dynamic range, D, is the ratio of the largest absorbance that can be measured reliably, $\alpha_{MAX}$, to the smallest absorbance that can be measured reliably, $\alpha_{MIN}$; $D=\alpha_{MAX}/\alpha_{MIN}$. For fixed optical path lengths, D also determines the range of concentration or number density that can be measured. The largest measurable absorbance, $\alpha_{MAX}$, is, in part, limited by the smallest value of I that can be distinguished from zero. For example, an absorbance of 10 corresponds to only $e^{-10}=0.005\%$ of the incident light exiting from the sample. Furthermore, reliably distinguishing an absorbance of 10 from absorbances of 9 or 11 requires distinguishing 0.002% transmission from 0.012% and 0.005% transmission, respectively. The requirements are further constrained by the need to also measure $I_0$ when it is 20,000 times larger than I. Few optical detectors can operate over that range of light intensity. It would be possible to combine multiple detectors, each having a different sensitivity range, to cover the full absorbance dynamic range; but, this combination would be expensive to implement and likely to need frequent calibration.

Figure 1:
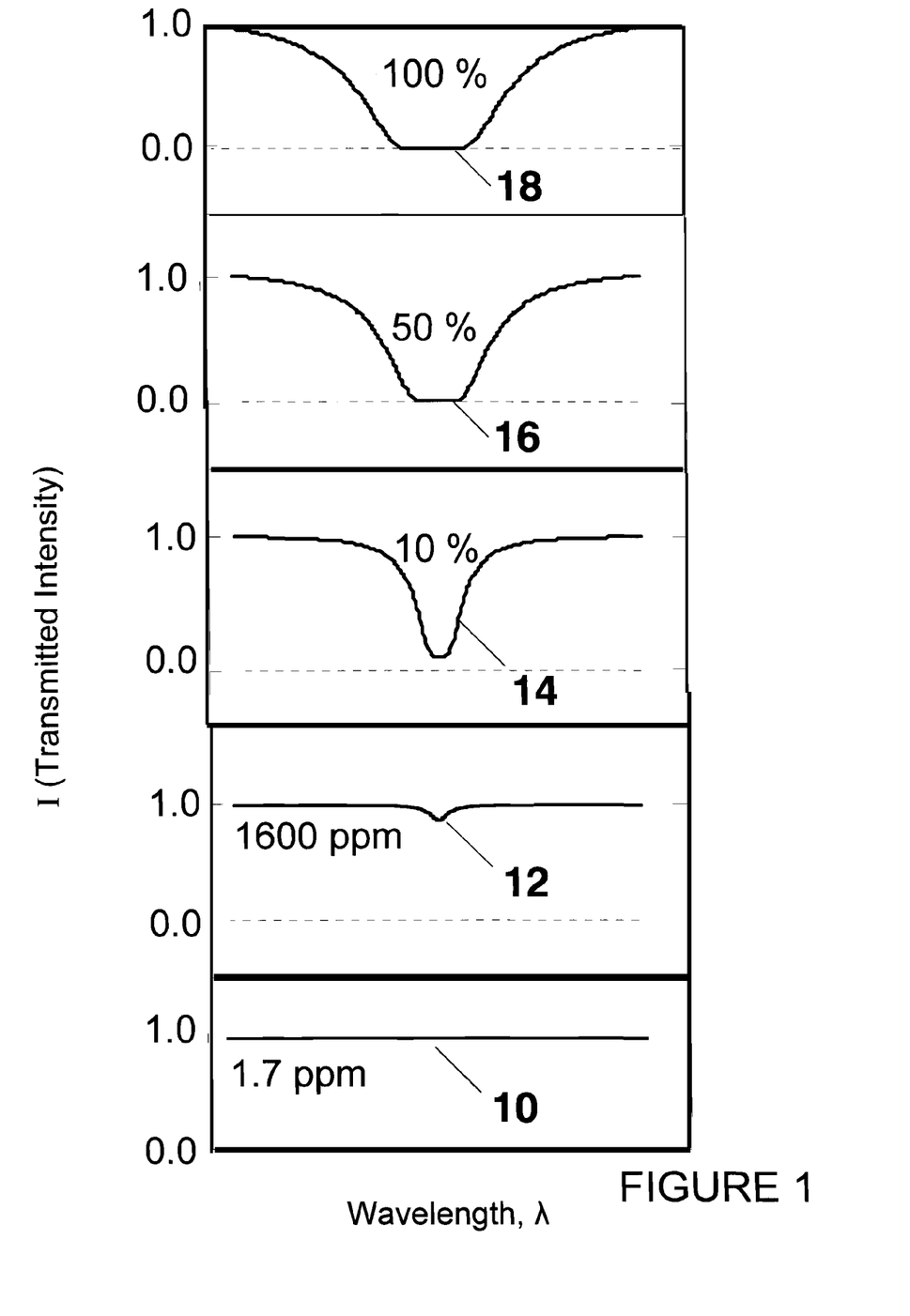
FIG. 1 is a drawing of the changes in optical transmission spectral line shapes with increasing sample absorbance, and shows the onset of optically thick conditions.

Samples having large absorbances, i.e., $\alpha>>1$, are identified as optically thick or optically dense. The terms are used interchangeably. A complete description of the spectroscopy of optically thick samples requires an elaboration of Beer's Law to include the shape of the absorption feature, $$\alpha(\nu)=S(T)\cdot g(\nu,T,P,\chi_i)\cdot n\cdot l,$$

where $\nu$ is the optical frequency (inversely proportional to wavelength), S is the line strength, T the temperature, P the pressure, and $O_i$ the species mole fraction. The line shape function, g, is a maximum at the center of the absorption line and is a Voigt function for most gases near atmospheric pressure. The Voigt function is a convolution of Doppler and Lorentzian line shapes as is well known in the art. Numerical methods for computing Voigt functions are given by Drayson (S. R. Drayson, "Rapid Computation of the Voigt Profile," J. Quant. Specrosc. Radiat. Transfer 16, 611-614 (1976)) and Hui et al. (A. K. Hui, B. H. Armstrong, and A. A. Wray, "Rapid Computation of the Voigt and Complex Error Functions," J. Quant. Spectrosc. Radiat. Transfer 19, 509-516 (1978)). FIG. 1 is a series of transmission spectra showing the effect of increasing peak absorbances. The spectra were calculated using the HITRAN data base (Rothman, L. S., Jacquemart, D., et al., "The HITRAN 2004 Molecular Database," J. Quant. Spectrosc. Radiat. Trans. 92, 139-204 (2005)) to simulate the methane absorption line at 1654 nm, and assume a 1 m long optical path. At the lowest methane concentration 10 corresponding to the average ambient atmospheric methane concentration, 1.7 ppm, the transmission appears to be 1.0 for all wavelengths. The absorbance, 3.7H $10^{-5}$, corresponds to a transmission of 0.99996 at line center and cannot be observed on the scale of the figure. Increasing the concentration to 10%, trace 14, increases the absorbance to 2.1, and the transmission is only 13%. By 50% the sample is optically thick, trace 16; the peak absorbance is 10.9 and the transmission reduced to nearly zero at 0.000019. Increasing the concentration further to 100% broadens the transmission line shape 18 and widens the wavelength region over which the sample is optically thick.

Hirshfeld describes one approach for obtaining quantitative absorption spectra of optically thick samples (T. Hirschfeld, "Dynamic range improvement in Fourier transform infrared spectroscopy," J. Am. Chem. Soc. 50, 1227-1228 (1978)). He teaches simultaneous measurements of a given sample using two different path lengths to solve the problem of optically dense samples. Garver et al. describes a spectrometer having a plurality of path lengths (T. M. Garver, D. G. Jenkins, and A. Riser, "Multiple pathlength spectrometer," U.S. Pat. No. 6,643,016, issued Nov. 4, 2003), with each path length illuminated by light having a narrow wavelength range and the length optimized for the anticipated absorbance within that wavelength range.

Sample cells having widely variable path lengths are commercially available. Examples include the model A134 gas cell from Bruker Optics that can be adjusted for optical paths between 3.2 and 40 m. The cell uses White's design (White, J. U., "Long Optical Paths of Large Aperture," *J. Opt. Soc. Am.*, vol. 32, pp 285-288 (May 1942)) for a multiple pass optical cell, and is expensive and requires careful adjustment to change the optical path length. Accessories for Perkin Elmer's BX series of Fourier transform infrared spectrometers include Teflon spacers available in thicknesses between 0.025 and 0.5 mm that are used to define the optical path length between entrance and exit windows. Changing the path length, however, requires first removing the sample and dismantling the cell.

A sub-specialty of optical spectroscopy known as saturation spectroscopy (S. Svanberg, G.-Y. Tan, T. P. Duffey, W.-M. Du, T. W. Hansch and A. L. Schawlow, "Saturation spectroscopy for optically thick atomic samples," J. Opt. Soc. Am. B 4, 462-469 (1987); H. Chen, H. Li, Y. V. Rostovtsev, M. A. Gubin, V. A. Sautenkov, and M. O. Scully, "Near-infrared saturation spectroscopy of cesium molecules using a diode laser," J. Opt. Soc. Am. B 23, 723-726 (2006)) is a non-linear spectroscopic technique for investigating fine structure in atomic spectra and takes advantage of unusual optical properties of optically thick gaseous samples. This approach is not suitable for molecular species, nor does it provide quantitative information about species concentrations or number densities.

At the other extreme, the minimum detectable absorbance, $\alpha_{MIN}$, is determined by the largest value of I that can be reliably distinguished from $I_0$. For nearly all light sources, including lasers and lamps, distinguishing I from $I_0$ is limited by the amplitude noise of the light source. This noise is commonly known as excess noise, pink noise, source noise, and 1/f noise. The noise power spectrum maximizes at frequencies near DC, and decreases with increasing frequency until fundamental noise sources including laser-detector shot noise and detector thermal noise are dominant. Researchers, including the Inventors, have demonstrated spectroscopic techniques that minimize the deleterious effects of excess noise by shifting the measurement bandwidth from frequencies near DC to those where excess noise is unimportant. Minimum detectable absorbances of $\alpha_{MIN}$. $10^{-5}$ for a one second measurement are typically achieved using wavelength tunable, continuous wave diode lasers as light sources. Pertinent techniques include wavelength modulation spectroscopy (J. Reid, M. El-Sherbiny, B. K. Garside, and E. A. Ballik, "Sensitive limits of a tunable diode laser spectrometer with application to the detection of NO2 at the 100-ppt level," Appl. Opt. 19 3349 (1980); J. A. Silver, "Frequency Modulation Spectroscopy for Trace Species Detection: Theory and Comparison Among Experimental Methods," Appl. Opt. 31, 707 (1992); and, D. S. Bomse, A. C. Stanton and J. A. Silver, "Frequency Modulation and Wavelength Modulation Spectroscopies: Comparison of Experimental Methods Using a Lead-Salt Diode Laser," Appl. Opt. 31, 718 (1992)), frequency modulation spectroscopy (G. C. Bjorklund, "Method and device for detecting a specific spectral feature," U.S. Pat. No. 4,297,035, issued Oct. 27, 1981; G. C. Bjorklund, M. D. Levenson, W. Lenth, and C. Ortiz, "Frequency modulation (FM) spectroscopy," Appl. Phys. B 32, 145 (1983)), two-tone frequency modulation spectroscopy ("Frequency modulation spectroscopy using dual frequency modulation and detection," U.S. Pat. No. 4,765,736; issued Aug. 23, 1988; D. E. Cooper and T. F. Gallagher, "Double Frequency Modulation Spectroscopy", Appl. Opt. 24, 1327-1333 (1985); J. A. Silver and A. C. Stanton, "*Two-Tone Optical Heterodyne Spectroscopy Using Buried Double Heterostructure Lead-Salt Diode Lasers*," Appl. Opt. 27, 4438 (1988)), rapid scan absorption spectroscopy (Aerodyne), and noise canceller methods (P. C. D. Hobbs, "Noise cancelling circuitry for optical systems with signal dividing and combining means," U.S. Pat. No. 5,134,276, issued Jul. 28, 1992; P. C. D. Hobbs, "Ultrasensitive laser measurements without tears," Appl. Opt. 36, 903 (1997)).

The high sensitivity techniques assume absorbances small enough that Beer's Law can be approximated as follows:

$$\frac{\Delta I}{I_0} = \left(\frac{I_0 - I}{I_0}\right) = 1 - \exp(-\alpha)$$
$$\approx \alpha \text{ (for } \alpha \ll 1)$$

Figure 2:
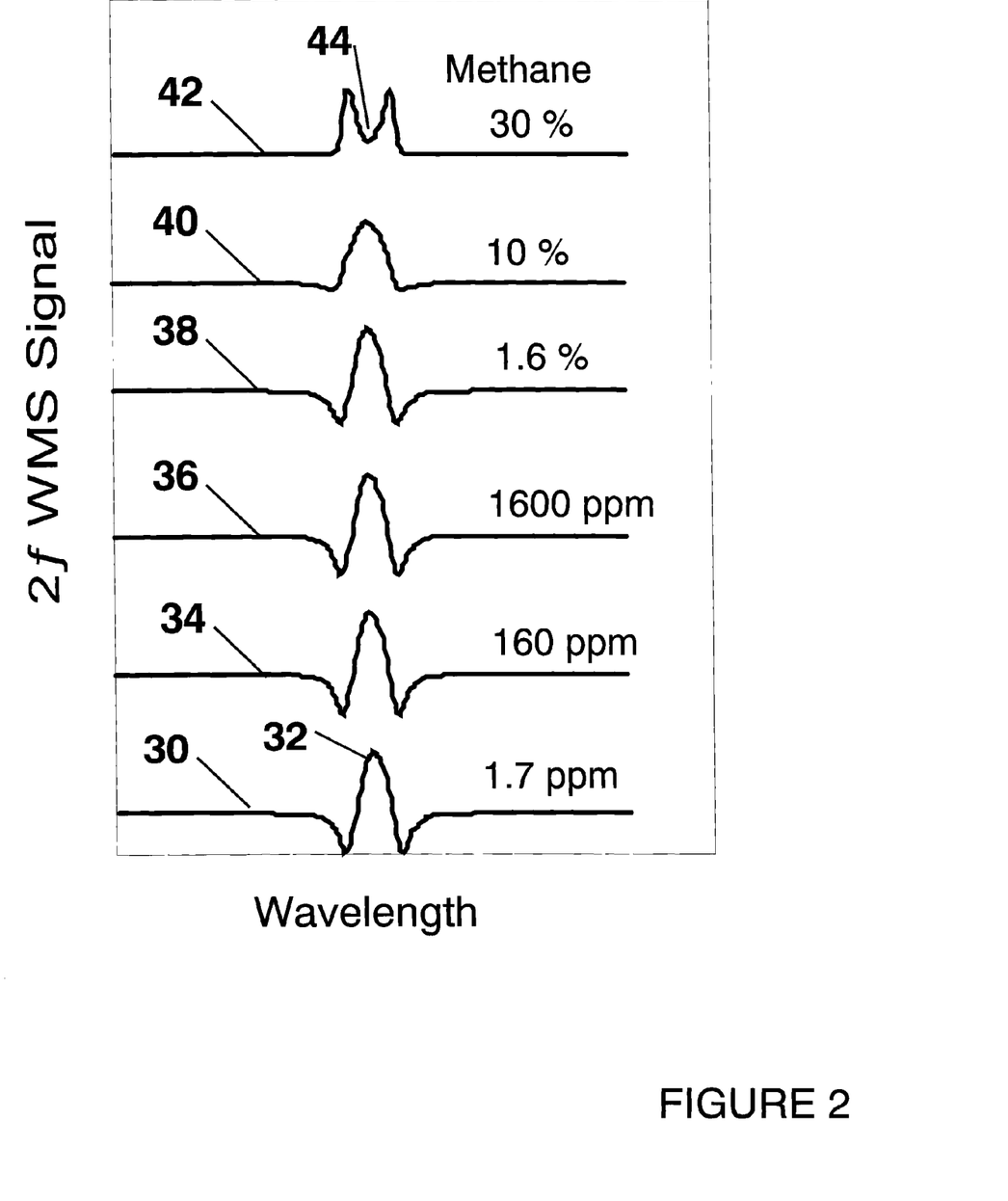
FIG. 2 is a drawing of the changes in wavelength modulation spectral line shapes with increasing sample concentration and absorbance.

In this case, the absorbance, $\alpha$, is linearly proportional to n, the target species number density or concentration. Non-linearities become important as $\alpha$ exceeds ~0.1. FIG. 2 shows changes in wavelength modulation spectral line shapes using second harmonic (2f) detection for methane as the methane concentration increases. Amplitudes are scaled to unity. The spectra were calculated using HITRAN data base information and follow the procedure described by Silver (1992), and assume a 1 m optical path length. At the ambient atmospheric methane concentration, 1.7 ppm, the absorbance is 3.7 H $10^{-5}$, and the spectral line shape 30 looks similar in shape to the second derivative of the absorption line. The extremum 32 in the 2f spectrum occurs at the absorption line center. The 2f line shape remains nearly invariant (although the magnitude would increase) for concentrations up to about 1.6%, 38, corresponding to an optical absorbance of 0.35. Increasing the concentration by an additional order of magnitude results in a broader central peak and shallow side lobes 40. As the sample becomes optically thick ($\alpha$=10.5), there is nearly no light transmitted at the peak center, and the central lobe of the 2f spectrum disappears 44 leaving a significantly different spectral line shape 42. The 2f signal magnitudes are linearly proportional to concentration for $\alpha$<0.1, and become sub-linear at higher concentrations and at the highest concentrations are no longer monotonic. The non-linearity is strongest among spectra 38, 40, and 42. Increasing the methane concentration form 1.6% to 10%, a factor of 6.25, increases the 2f extremum by only 0.15. The next increase, from 10% to 30%, actually produces a drop in 2f magnitude as the largest parts of spectral line 42, the two side lobes, are half the size of the central lobe in the 10% concentration spectrum 40.

An embodiment of the instant invention is a natural gas leak detector having a methane concentration measurement range extending from the ambient atmospheric background concentration of about 1.7 parts per million to 100%. No known prior art exists in the areas of methane concentration measurements or natural gas leak detection that encompasses a similarly large measurement dynamic range. Griggs et al.

(M. Griggs, L. L. Action, and G. D. Hall, "Method and apparatus for accurate remote monitoring of gases," U.S. Pat. No. 4,520,265, issued May 28, 1985) describe optical measurements using a narrow band optical interference filter centered at the Q-branch of the methane band at 3.3 μm that is combined with gas correlation cells and a separate measurement of light intensity at 10 μm to determine methane average concentrations along an open path in order to identify methane plumes resulting from natural gas leaks. The light source is thermal emission from background terrain or buildings. Applications include open path measurements from airborne platforms or ground vehicles. The largest optical absorbance is about 6. Although Griggs describes the interference filter as "narrow band," its wavelength pass band is large compared with the width of methane absorption lines having absorbances below ~2.

Heath Consultants, Inc. (Houston, Tex.) sells two optical methane sensors. Their Optical Methane Detector or OMDյ has a fixed open path approximately 1 meter long that has a manufacturer's stated measurement range of 1 to 200 ppm. This dynamic range is 5000 times smaller than the dynamic range of the instant invention. The other, called Remote Methane Leak Detector or RMLDյ, is a hand-held, point-and-shoot, diode laser based device with a measurement range of 0 to 99,999 ppm-m. The unit ppm-m is known as column density and is the product of the average gas concentration along an optical path and the optical path length; i.e., it is the product nl. Rutherford (J. M. Rutherford, "Method and apparatus for laser-based remote methane leak detection," U.S. Pat. No. 7,075,653; issued Jul. 11, 2006) describes the RMLDյ. The instrument uses only one spectroscopic method, wavelength modulation spectroscopy, and employs an open optical path of varying length. A handheld optical transceiver emits light from a near-infrared diode laser (nominal wavelength 1654 nm) and collects light that is back scattered from or reflected from an object illuminated by the outgoing beam. The optical path length is double the distance from the transceiver to the object. This length changes as the operator moves the transceiver. A visible laser beam aligned with the near-infrared laser helps the operator to determine the location of the near-infrared beam. Changes in the optical path length result in concomitant changes in the methane column density due to the integrated absorbance by atmospheric background methane alone the optical path. Data analysis methods emphasize identifying sudden changes in methane column density exceeding the signal due to the background concentration as indicative of a natural gas leak. In contrast, the instant invention samples gas into an optical cell having a fixed and constant optical path length, and measures absolute methane concentrations between nominally 1.7 ppm and 100%. The present invention does not rely on changes in column density where the starting column density is uncertain.

In favorable cases, it is possible to use two or more spectral features having substantially different line strengths to span a large dynamic range as demonstrated by Zondlo et al. (Zondlo, M. A., J. A. Silver, D. S. Bomse, and M. E. Paige, "VCSEL-based hygrometer for the High-performance Instrumented Airborne Platform for Environmental Research (HIAPER)", American Chemical Society National Meeting, Paper No. 302, Analytical Chemistry, Analytical Chemistry in the Atmospheric Sciences, Mar. 14, 2005, San Diego, Calif.) for atmospheric water vapor measurements. Zondlo's approach does, however, require a highly prescribed combination of target species spectroscopic properties, light source wavelength coverage, and freedom from interfering species. These requirements are more easily met for water vapor than for other species because water vapor occurs at relatively high concentrations and has a plethora of absorption bands throughout the mid- and near-infrared wavelength regions.

Currently used natural gas leak detection methods employ up to three separate devices to span natural gas concentrations from ~1 ppm to 100%. The technology includes high- and low-sensitivity flame ionization detectors, and a thermal conductivity measurement for the largest concentrations.

BRIEF SUMMARY OF THE INVENTION

The present invention is of an optical spectroscopy apparatus and method for measurement of species concentration, number density, or column density, comprising: emitting light from a laser light source; receiving light via a fixed length optical path from the source and containing a species to be detected; receiving light via a detector at an end of the path; determining one or more of species concentration, number density, and column density via signal processing electronics connected to the detector; and switching between a plurality of operational modes measuring a same absorption feature of the species depending on measured absorbance. In the preferred embodiment, a beamsplitter, a sample container containing the species, a detector receiving light from the sample container, and signal-processing electronics are employed to establish linelocking of the absorption feature. The path preferably comprises a multiple pass optical cell. Switching is preferably between at least three operational modes, most preferably wherein a first operational mode is selected from wavelength modulation spectroscopy, frequency modulation spectroscopy, two-tone frequency modulation spectroscopy, cavity ringdown spectroscopy, and rapid-scan direct absorption spectroscopy, a second operational mode determines absorbance from a measurement of width of the absorption feature, and a third operational mode comprises direct absorption spectroscopy. Where the species is methane, it is preferred that the first operational mode operates at absorbances less than approximately 0.1, the second operational mode operates at absorbances greater than approximately 0.3, and the third operational mode operates at absorbances between approximately 0.1 and 0.3. Modulation is turned off for the second and third operational modes, a peak of a direct absorption spectrum provides a wavelength set point for the second and third operational modes, and the signal processing electronics adjusts temperature of the source for the first operational mode. Water is another species ably detected by the present invention.

A primary object of the present invention is to measure optical absorbances over large dynamic ranges.

Another object of the invention is to make possible inexpensive natural gas leak detectors capable of quantitative methane concentration measurements between normal atmospheric background values and 100%.

Another object of the invention is to replace existing natural gas leak detection systems that require a plurality of measurement devices with a single device.

Another object of the invention is to replace flame ionization detectors that pose an explosion hazard with sensors and analyzers that are safer and can be made intrinsically safe.

Another object of the invention is to make possible inexpensive gas sensors and analyzers capable of concentrations measurements over a wide dynamic range.

Another object of the invention is to provide a generally useful control procedure for sensors and analyzers based on optical absorbance that must accommodate large variations in sample absorbance.

Another object of the invention is to improve the performance of single beam optical absorbance spectrometers.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is of methods and apparatus for quantitative measurement of species concentration, number density, or column density over an extensive range using optical spectroscopy and a sample region of fixed optical path length. The measured species can be a solid, liquid, or gas. Two or more spectroscopic methods are used to cover the full measurement dynamic range. A first spectroscopic method is selected for high sensitivity quantitative absorbance measurements for sample absorbances that are typically smaller than $10^{-1}$. A second method spans sample absorbances that can exceed ~4. A third method may be employed to cover an intermediate absorbance range between those covered by the first and second methods. Spectroscopic method selection and corresponding control of the spectroscopic light source and processing of the detector output are performed by a computer specifically programmed for these tasks. The preferably computer implemented algorithm includes selection points that determine when to switch between methods. Hysteresis in switching points prevents oscillation between methods as sample absorbances cross a transition point. This invention prefers a single, fixed sample optical path and all spectroscopic methods measure the same absorption feature.

Spectroscopic first methods include but are not limited to wavelength modulation spectroscopy, frequency modulation spectroscopy, two-tone frequency modulation spectroscopy, noise canceller methods, cavity ringdown spectroscopy, and rapid-scan direct absorption spectroscopy. The second spectroscopic method, used for optically thick samples, determines the sample absorbance from a measurement of a width of the absorption spectrum. The width is the optical transmission at a wavelength having a selected difference from the wavelength of the center of the absorption feature. Third spectroscopic methods include but are not limited to direct optical absorbance spectroscopy.

Useful spectroscopic light sources include but are not limited to lasers such as wavelength tunable lasers such as diode lasers (including external cavity diode lasers), dye lasers, and optically pumped solid-state lasers (including diode pumped solid state lasers); light sources obtained using non-linear optical methods such as difference frequency generation, sum frequency generation, harmonic generation, and optical parametric oscillation; broad band light sources such as lamps, light emitting diodes and thermal emitters in combination with wavelength selection optics such as gratings, prisms, and interferometric devices.

The spectrometer detector is a device that converts in a well-defined manner light beam intensity to a voltage or current, and has a response time suitable for all spectroscopic methods used by the spectrometer. Suitable detectors include but are not limited to photodiodes and photomultipliers.

Figure 3:
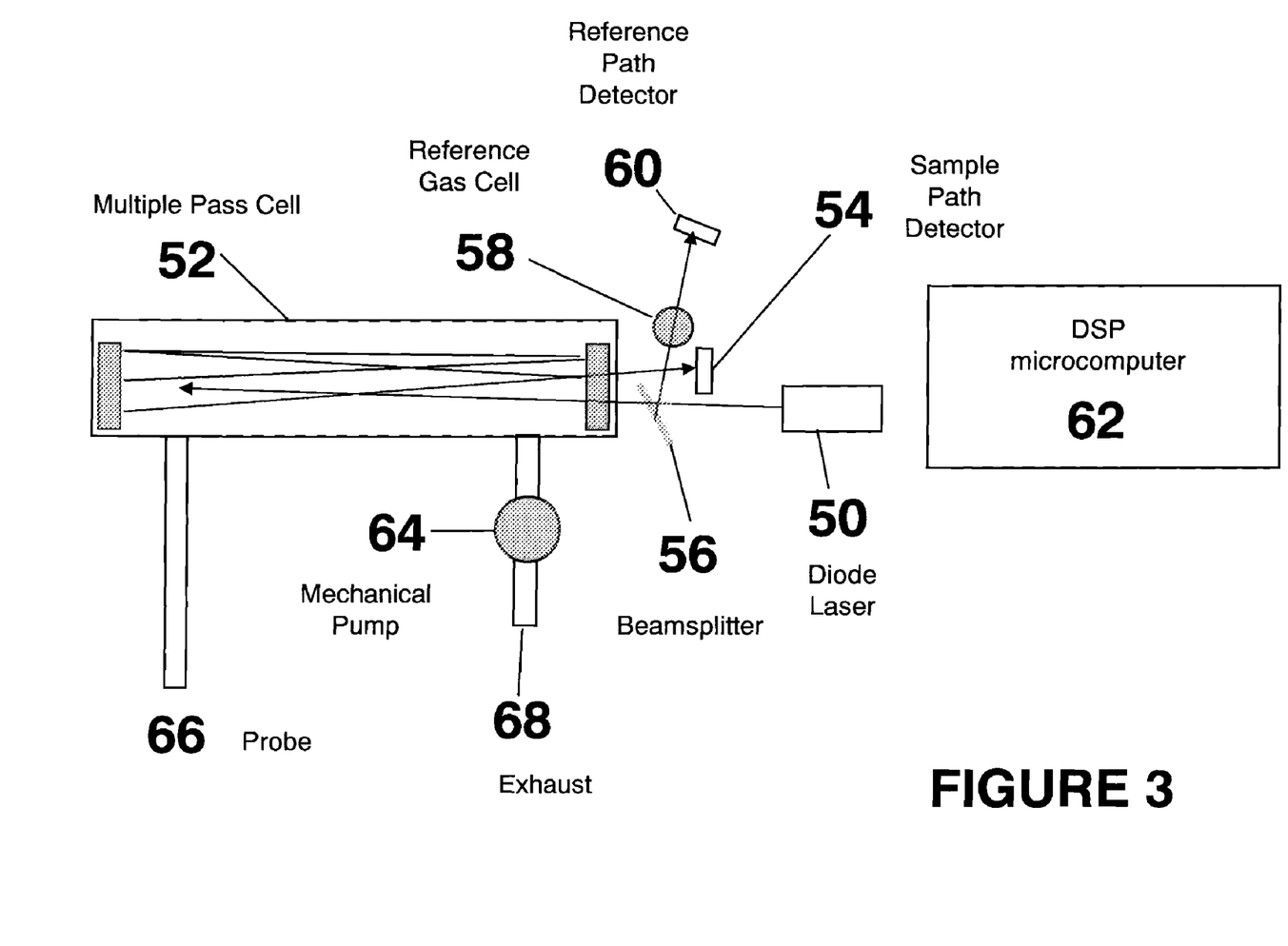
FIG. 3 is a schematic drawing of an embodiment of the present invention preferred for use in methane detection.

The illustrative embodiment is a device used to locate natural gas leaks, shown in FIG. 3. It comprises a near-infrared diode laser 50 having a wavelength tuning range encompassing at least one absorption line due to methane in the wavelength region around 1654 nm, a compact multiple pass optical cell 52 having an optical path length of about 1 m, and an InGaAs photodiode detector that receives the sample path beam after it exits the sample cell 54. A small portion of the laser light is directed by a beam splitter 56 through a portion of methane in a reference cell 58 and then onto a second InGaAs photodiode 60. Output from the second photodiode is used to maintain the laser wavelength scan at the selected methane absorption line. The laser temperature and current are controlled by a microcomputer 62 based on a digital signal processor (DSP). A miniature 15 cm$^3$ per second mechanical pump 64 draws air samples through a probe 66 and into the sample cell, and then exhausts the sample 68.

The multiple pass optical cell 52 preferably follows the Herriott's design (Herriott, D. R., et al., "Folded Optical Delay Lines," *Appl. Opt.*, vol. 4, No. 8, pp 883-889 (Aug. 1965)), and has a sample volume of 18 cm$^3$. The cell includes two 15 mm diameter, convex mirrors having 60 mm focal lengths, and placed 100 mm apart. Ten passes through the cell result in a 1.07 m total path length.

Figure 4:
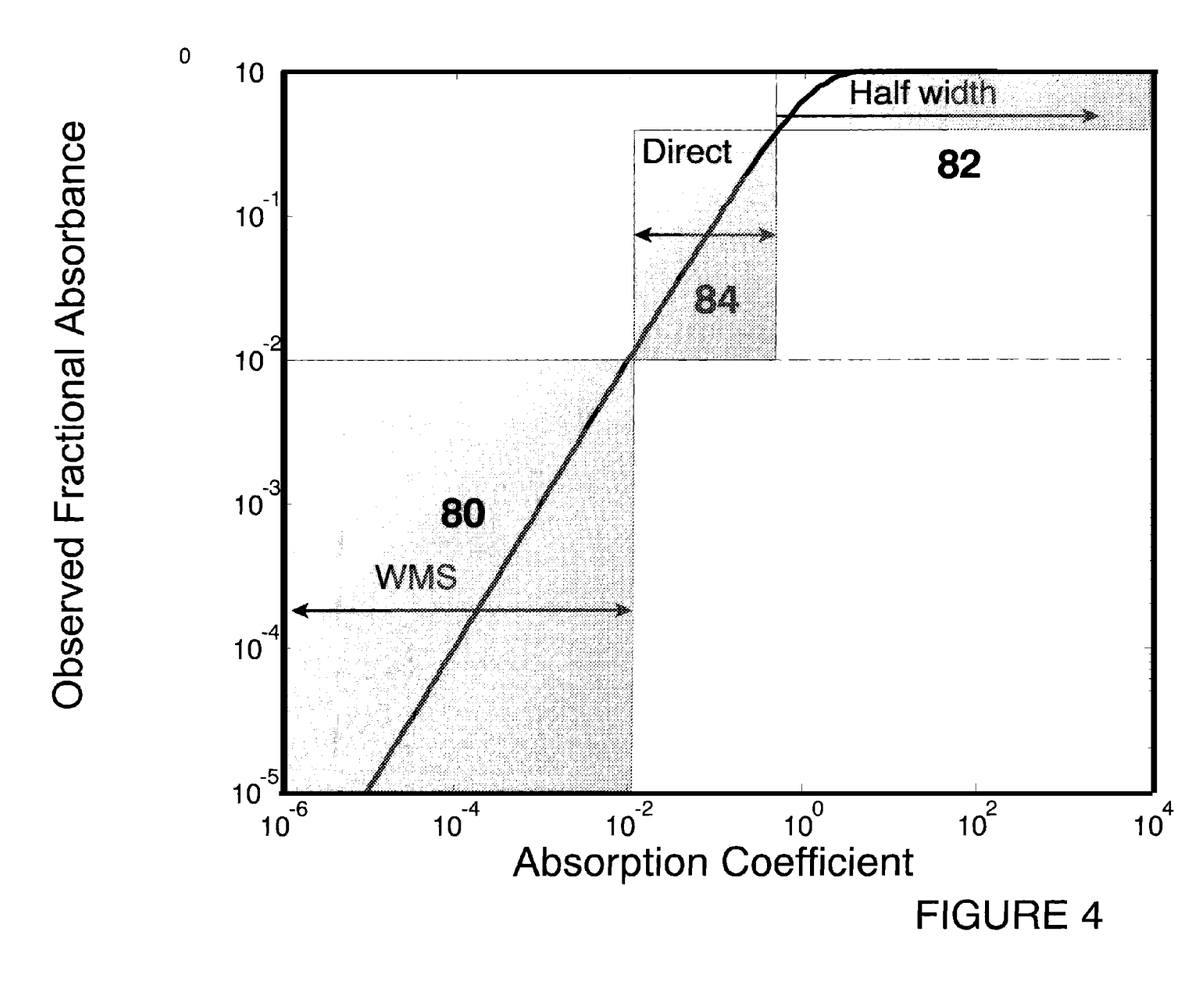
FIG. 4 is a graph showing the different detection regions as a function of absorbance.

FIG. 4 shows the absorbance ranges for the three spectroscopic methods used. The first spectroscopic method used 80 is wavelength modulation spectroscopy implemented by applying a periodic modulation to the laser current at a frequency of 250 kHz. Output from each InGaAs detector is demodulated using phase-sensitive demodulation electronics located on the microcomputer board. The resulting demodulated signals are acquired by the microcomputer using analog-to-digital converters, with the data acquisition synchronized with changes in the laser wavelength sweep current. This sequence generates wavelength modulation spectra of the sample and the reference. Wavelength modulation spectroscopy is used for sample absorbances less than 0.01. Calibrations show accuracy of better than 2% in methane concentration or mole fraction.

The absorbance due to methane in the sample cell and, therefore, the methane concentration in the sample, is computed by the microcomputer using the amplitudes of the sample wavelength modulation spectrum. The computed methane gas concentration is reported to the user. The concentration is also compared with set points for switching among the spectroscopic methods.

The second method is measurement of the optical transmission at a selected wavelength displaced from the center of the methane absorption peak. The second measurement method is used for absorbances exceeding 0.3 (about 1% methane). The observed transmission is compared with values obtained by calibration or calculation to determine the methane concentration. Implementing the second method includes turning off the laser current modulation and digitizing the InGaAs photodiode outputs directly without using the demodulation electronics. The selected wavelength used for the transmission measurement need not be specified absolutely. It can be determined using a direct absorption spectrum having an absorbance of about 2. The width of that spectrum is used to determine the wavelength scan rate of the laser with changing current, and the selected wavelength for the second method measurements is computed as a fixed multiple of the direct absorption spectrum width.

In the preferred embodiment, the third method is direct absorption spectroscopy, and is used for sample absorbances between 0.1 and 0.3. The laser modulation is switched off, and the InGaAs photodiode outputs are digitized directly by the microcomputer. The peak absorbance is calculated by converting by applying Beer's Law to the optical transmission spectrum obtained by scanning the diode laser wavelength across the methane absorption line.

Spectra of the reference gas are used to maintain the methane absorption peak at or close to the center of the laser wavelength scan range. For the first spectroscopic method, the wavelength modulation spectrum, obtained by demodulating the detector output at twice the modulation frequency, has an extremum at the methane peak center. The microcomputer program compares the position of that extremum with the desired peak position, and adjusts the laser temperature to shift the laser wavelength scan range accordingly. Odd harmonic detection (e.g., 1f, 3f . . . ) of the reference spectra results in zero crossings at the line center that can also be used to locate the peak position. For the second and third methods, the peak of the direct absorption spectrum of the reference gas provides the wavelength set point.

Figure 5:
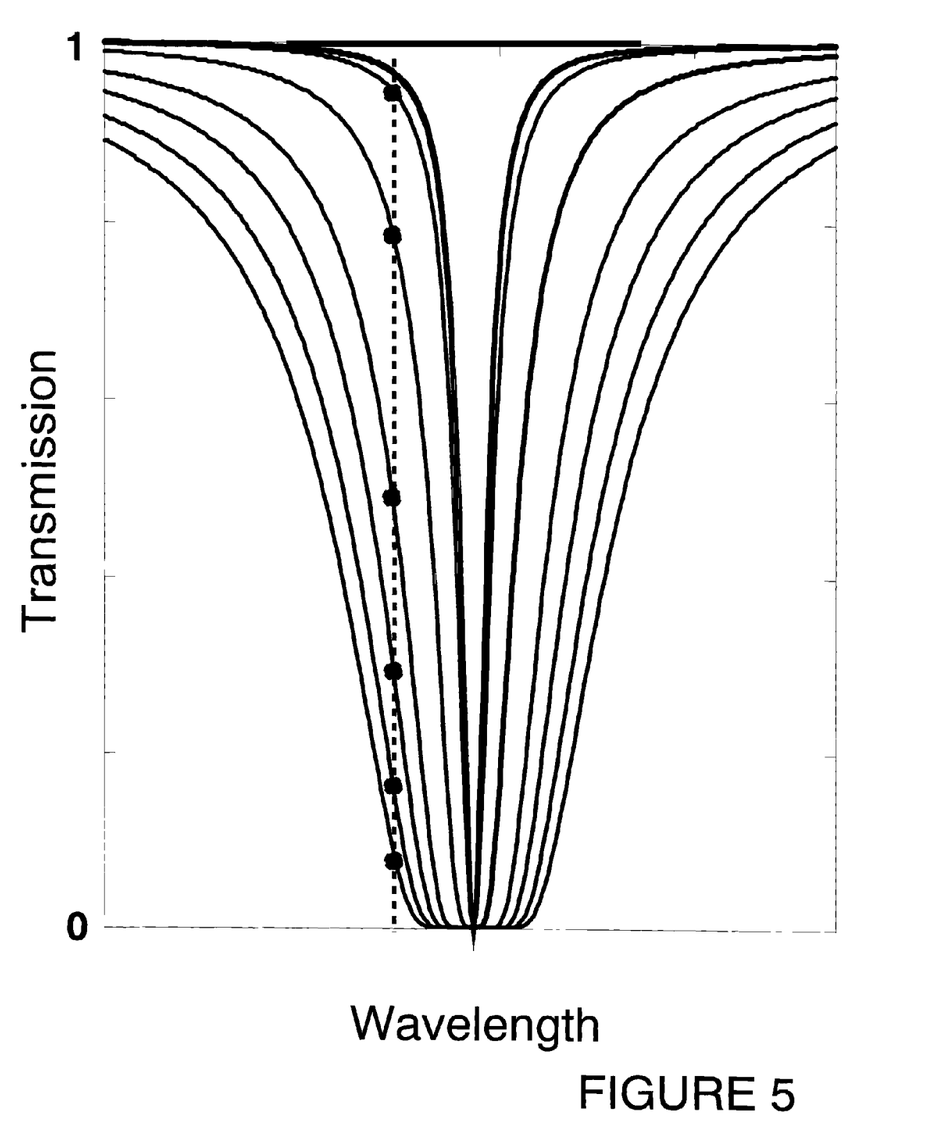
FIG. 5 is a drawing of normalized transmission line shapes for varying absorbances.

FIG. 5 shows the changes in methane transmission line shapes with changing methane concentration or mole fraction for the absorption line at 1654 nm. All spectra are normalized to unity peak signal. The changes in peak width are readily apparent. In the preferred embodiment, the device is calibrated for optically thick samples by first filling the multiple pass cell with pure (100%) methane, and locating the wavelength or optical frequency displacement from the line center (as indicated by the spectrum of the reference gas) where the observed transmission is 10%. Next, the transmission at that selected wavelength or optical frequency is measured for a series of calibration gas mixtures exhibiting transmission between about 90% and 10%. The vertical dotted line in FIG. 5 identifies the selected wavelength and the filled circles are the observed transmissions for the corresponding calibration gases. The resulting data (transmission at selected wavelength vs. concentrations) are fit to a second order polynomial 100, FIG. 6. Parameterization of the data set enables rapid computation of sample concentration from a measurement of transmission at the selected wavelength.

Figure 6:
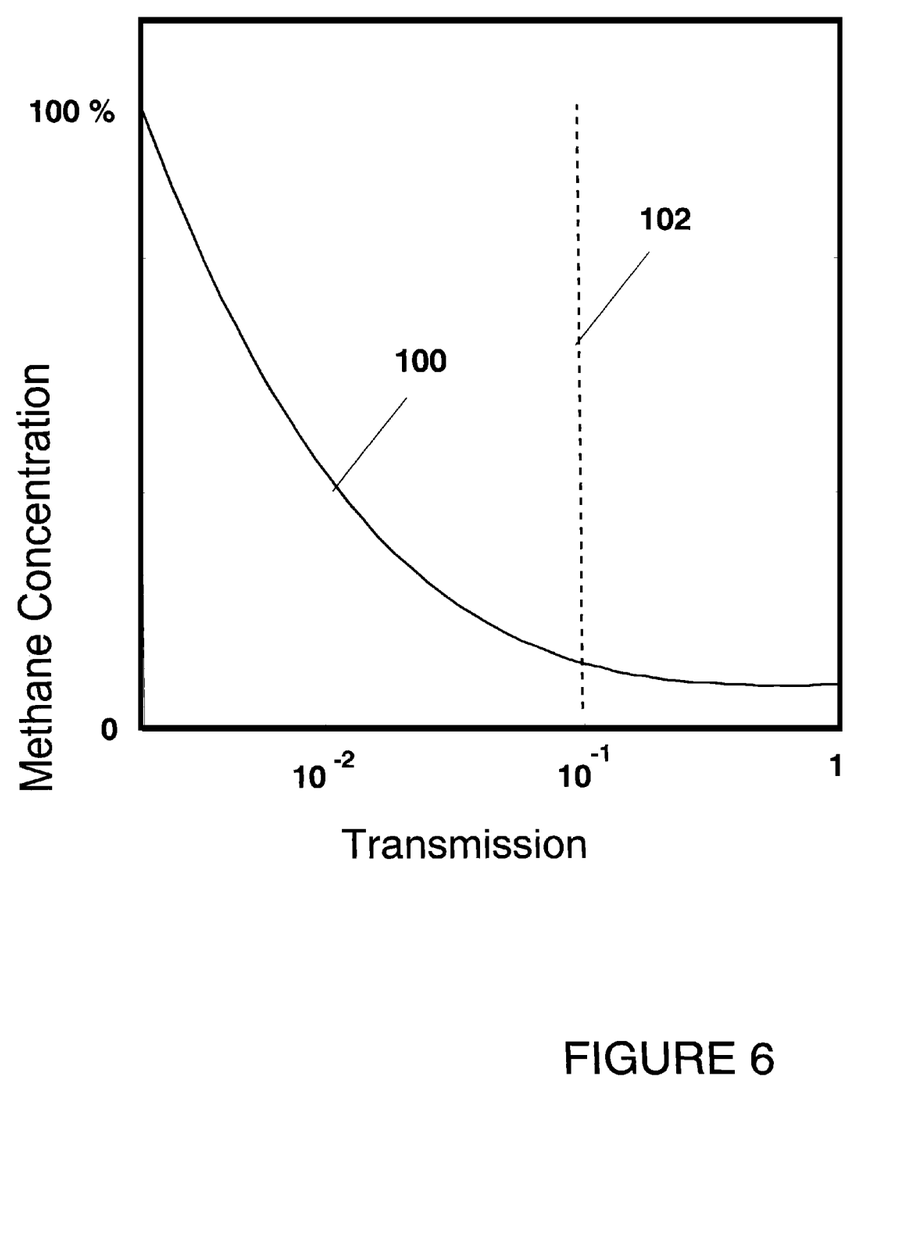
FIG. 6 is a graph showing the quadratic fit to the transmission line shape as a function of target species mole fraction and absorption coefficient.

Note that the trace 100 in FIG. 6 shows significant sensitivity to gas concentration for concentrations above approximately 10%. The parameterization does not give accurate results for lower concentrations; hence, the use of direct absorption spectroscopy (the third spectroscopic method). The preferred transition point is about 10% transmission, 102.

In the preferred embodiment, the methane concentration measurement accuracy is further improved by correcting the spectroscopic results for changes due to variations in ambient temperature and pressure. Temperature and pressure effects are dominated by changes in the gas number density within the optical cell, and can be corrected using the ideal gas law. Pressure changes also produce subtle effects on absorption line widths, and are corrected by calibration. As a result, commercial implementations of the preferred embodiment provide reliable operation at temperatures between −40 and +50 EC and altitudes from sea level to over 2000 m.

Measured methane concentrations or mole fractions are reported to the user by the DSP microcomputer. Typical update rates are 1 Hz.

A second embodiment of the invention is an airborne hygrometer for measuring water vapor concentrations in the atmosphere at altitudes ranging from about sea level to the upper troposphere. Water vapor concentrations vary by about six orders of magnitude, from 5.6% down to about 1.5 parts per billion over this range of conditions. Corresponding dew/frost points range from +35 to −110 EC. This embodiment uses a multiple pass cell that is open to the atmosphere and provides a sample path length of about 4 m. The wavelength tunable light source is a vertical cavity surface emitting diode laser operating at a wavelength near 1855 nm. Laser control and signal processing electronics are similar to those described in the preferred embodiment. The omnipresence of water vapor in the atmosphere eliminates the requirement for a separate reference cell and its related beam splitter and photodiode detector. There is sufficient sample path signal to use for laser wavelength stabilization.

Additional embodiments include modifying the hygrometer for less extreme conditions by substituting a diode laser operating near 1394 nm or 942 nm for the 1855 nm device. Advantages of these changes include lower costs for the shorter wavelength lasers and their corresponding photodiode detectors.

A third embodiment is a diode laser hygrometer used to monitor the progress of gas evacuation or gas substitution within industrial apparatus such as a semiconductor manufacturing device. Measuring the change in water vapor concentration determines the effectiveness of the gas removal or exchange process for systems in which water vapor is an unwanted component of the gas within the manufacturing device. This type of measurement is particularly important for semiconductor processing because many standard processing methods (such as chemical vapor deposition methods and plasma etching methods) are adversely affected by trace amounts of residual water vapor.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An optical spectroscopy apparatus for measurement of species concentration, number density, or column density, said apparatus comprising:

a laser light source;

a single fixed length optical path receiving light from said source and containing a gaseous species to be detected;

a detector receiving light at an end of said path; and signal processing electronics connected to said detector; and wherein said apparatus has a plurality of operational modes measuring a same absorption feature of the species and wherein said apparatus switches between modes depending on measured absorbance.

2. The apparatus of claim 1 additionally comprising a beamsplitter, a sample container containing the species, a detector receiving light from the sample container, and signal-processing electronics establishing linelocking of said absorption feature.

3. The apparatus of claim 1 wherein said path comprises a multiple pass optical cell.

4. The apparatus of claim 1 wherein said apparatus has at least three operational modes.

5. The apparatus of claim 4 wherein:

a first operational mode is selected from the group consisting of wavelength modulation spectroscopy, frequency modulation spectroscopy, two-tone frequency modulation spectroscopy, cavity ringdown spectroscopy, and rapid-scan direct absorption spectroscopy;

a second operational mode determines absorbance from a measurement of width of the absorption feature; and a third operational mode comprises direct absorption spectroscopy.

6. The apparatus of claim 5 wherein the species is methane.

7. The apparatus of claim 6 wherein said first operational mode operates at absorbances less than approximately 0.1, said second operational mode operates at absorbances greater than approximately 0.3, and said third operational mode operates at absorbances between approximately 0.1 and 0.3.

8. The apparatus of claim 5 wherein modulation is turned off for said second and third operational modes.

9. The apparatus of claim 5 wherein a peak of a direct absorption spectrum provides a wavelength set point for said second and third operational modes.

10. The apparatus of claim 5 wherein said signal processing electronics adjusts temperature of said source for said first operational mode.

11. The apparatus of claim 5 wherein the species is water vapor.

12. An optical spectroscopy method for measurement of species concentration, number density, or column density, the method comprising the steps of:

emitting light from a laser light source;

receiving light via a single fixed length optical path from the source and containing a gaseous species to be detected;

receiving light via a detector at an end of the path;

determining one or more of species concentration, number density, and column density via signal processing electronics connected to the detector; and switching between a plurality of operational modes measuring a same absorption feature of the species depending on measured absorbance.

13. The method of claim 12 additionally comprising employing a beamsplitter, a sample container containing the species, a detector receiving light from the sample container, and signal-processing electronics to establish linelocking of the absorption feature.

14. The method of claim 12 wherein the path comprises a multiple pass optical cell.

15. The method of claim 12 wherein the switching step switches between at least three operational modes.

16. The method of claim 15 wherein:

a first operational mode is selected from the group consisting of wavelength modulation spectroscopy, frequency modulation spectroscopy, two-tone frequency modulation spectroscopy, cavity ringdown spectroscopy, and rapid-scan direct absorption spectroscopy;

a second operational mode determines absorbance from a measurement of width of the absorption feature; and a third operational mode comprises direct absorption spectroscopy.

17. The method of claim 16 wherein the species is methane.

18. The method of claim 17 wherein the first operational mode operates at absorbances less than approximately 0.1, the second operational mode operates at absorbances greater than approximately 0.3, and the third operational mode operates at absorbances between approximately 0.1 and 0.3.

19. The method of claim 16 wherein modulation is turned off for the second and third operational modes.

20. The method of claim 16 wherein a peak of a direct absorption spectrum provides a wavelength set point for the second and third operational modes.

21. The method of claim 16 wherein the signal processing electronics adjusts temperature of the source for the first operational mode.

22. The method of claim 15 wherein the species is water vapor.

* * * * *

UNITED STATES PATENT AND TRADEMARK OFFICE
CERTIFICATE OF CORRECTION

PATENT NO. : 7,616,316 B1  Page 1 of 1
APPLICATION NO. : 11/679608
DATED : November 10, 2009
INVENTOR(S) : Joel A. Silver, Mark E. Paige and David S. Bomse It is certified that error appears in the above-identified patent and that said Letters Patent is hereby corrected as shown below:

Column 6, line 39, delete "0.3" and substitute --3.0--

Column 6, line 41, delete "0.3"and substitute --3.0--

Column 9, line 7, delete "0.3" and substitute --3.0--

Column 9, line 7, delete "1%" and substitute --10%--

Column 9, line 23, delete "0.3" and substitute --3.0--

Column 11, line 31, delete "0.3" and substitute --3.0--

Column 11, line 32, delete "0.3" and substitute --3.0--

Column 12, line 34, delete "0.3" and substitute --3.0--

Column 12, line 35, delete "0.3" and substitute --3.0--

Signed and Sealed this

Twenty-sixth Day of January, 2010

David J. Kappos
*Director of the United States Patent and Trademark Office*